United States Patent [19]

Warriner

[11] Patent Number: Plant 5,860

[45] Date of Patent: Jan. 20, 1987

[54] ROSE PLANT JACALE

[75] Inventor: William A. Warriner, Tustin, Calif.

[73] Assignee: Jackson & Perkins Company, Medford, Oreg.

[21] Appl. No.: 730,152

[22] Filed: May 3, 1985

[51] Int. Cl.[4] ..... A01H 5/00

[52] U.S. Cl. ..... Plt./22

[58] Field of Search ..... Plt./22

*Primary Examiner*—Robert E. Bagwill

*Attorney, Agent, or Firm*—Manford R. Haxton

[57] ABSTRACT

A floribunda rose variety having compact, upright plant habit, large blooms of light pink, white and pale yellow blend, distinct fragrance and relatively large, mildew resistant, foliage.

1 Drawing Figure

1

This present invention relates to a new and distinct variety of rose plant of the floribunda class which was originated by crossing the unpatented variety Precilla with the variety Bridal Pink, U.S. Plant Pat. No. 2,851.

The primary objective of this breeding was to produce a new rose variety of the floribunda class with larger flowers than Bridal Pink and with some yellow pigments in the flower petals, compact plant. This objective was substantially achieved along with other desirable improvements as evidenced by the following unique combination of characteristics which are outstanding in the new variety and which distinguish it from its parents as well as from all other varieties of which I am aware:

1. Compact, upright plant habit;
2. Relatively large foliage;
3. Large flowers borne in clusters and singly on a stem;
4. Delicate coloring of pink, white and yellow;
5. Distinct fragrance;
6. Large flowers for the floribunda class; and
7. Reasonably good resistance to rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my rose cultivar with color in terminology in accordance with The Royal Horticultural Society Color Chart except where ordinary dictionary significance of color is indicated:

Parentage:

*Seed parent.*—Precilla, unpatented.

*Pollen parent.*—Bridal Pink, U.S. Plant Pat. No. 2,851.

Classification:

*Botanical.*—Rosa hybrid.

*Commercial.*—Floribunda.

2

FLOWER

Observations made from specimens grown in a greenhouse at Irvine, Calif., in February.

Blooming habit: Continuous.

Bud:

*Size.*—1¼" when petals start to unfurl.

*Form.*—Pointed ovoid.

*Color.*—When sepals first divide, Near Yellow 10D, outer petals overlaid with Orange Red 33C and 33B; when half blown, upper side of petals, base Near Yellow 10A blending to Near Yellow 10D, sometimes near white, overlaid after exposure to sunlight with Red 38A and 38B; lower side of petals, mostly Yellow 10C, darker near base, Yellow 10A.

*Sepals.*—Color: Yellow-green 145A. Three appendaged sepals lightly appendaged. Two unappendaged sepals, glandular edge.

*Receptacle.*—Color: Yellow Green 145A. Shape: Bowl. Size: Broad. Surface: Very slightly hairy.

*Peduncle.*—Length: Short. Surface: Prickly and glandular. Color: Light green. Strength: Stiff, erect.

*Opening.*—Slowly spiral open.

Open bloom:

*Size.*—Large. Average open size 4½"–5".

*Borne.*—Singly, in clusters, flat.

*Stems.*—Short, strong.

*Form.*—When first open, high center. Permanence: Retains its form to the end, outer petal edges slightly curled.

*Petalage.*—Number of petals under normal conditions: 30–35.

*Color.*—Center of flower: Upper side of petals, Yellow 10A; reverse side of petals, Yellow 10B. Base of petals, Yellow 10B. Outer petal color: Yellow 10D overlaid with Red 38C, darkening to Red 38A.

*Variegations.*—Color pattern may vary according to exposure to sunlight.

*Discoloration.*—General tonality at end of first day: Red pigmentation increases as flowers age.

*Fragrance.*—Strong.

Petals:

*Texture.*—Thick.

*Shape.*—Round.

*Form.*—Edges slightly quilled.

*Arrangement.*—Imbricated. Petaloids in center: few, large.
*Persistence.*—Drop off cleanly.
*Lastingness.*—On the plant, long. As cut flower, long.

Reproductive parts:
*Anthers.*—Medium. Color: Yellow. Arrangement: Regular around styles.
*Filaments.*—Color: Yellow.
*Pollen.*—Gold yellow.
*Styles.*—Color: White, tipped reddish.
*Stigmas.*—Color: Yellow.

PLANT

Form: Bush.
Growth: Vigorous, upright, compact; usually under 3′ in height.
Foliage: Number of leaflets on normal mid-stem leaves: 5.
*Size.*—Large.
*Quantity.*—Normal.
*Color.*—New foliage: Greyed Purple 187B. Old foliage: Green 147A.

Leaflets:
*Shape.*—Broadly oval.
*Texture.*—Leathery.
*Edge.*—Serrated.

*Serration.*—Single, small.
*Petiole.*—Rachis: Color: Reddish. Underside: Smooth, or with prickles.
*Stipules.*—Long, bearded.
*Disease resistance.*—Normally resistant to mildew, under normal growing conditions at Irvine, Calif.

Wood:
*New wood.*—Color: Light green. Bark: Smooth.
*Old wood.*—Color: Green. Bark: Smooth.

Prickles:
*Quantity.*—On main canes from base: Many. On laterals from main canes: Many.
*Form.*—Long, hooked downward.

Small prickles:
*Quantity.*—On main stalks, None. On laterals, None.

I claim:

1. A new and distinct variety of rose plant of the floribunda class, substantially as herein shown and described, characterized particularly as to novelty by the unique combination of its compact, upright plant habit, large blooms of light pink, white and pale yellow blend, distinct fragrance and relatively large, mildew resistant, foliage.

* * * * *

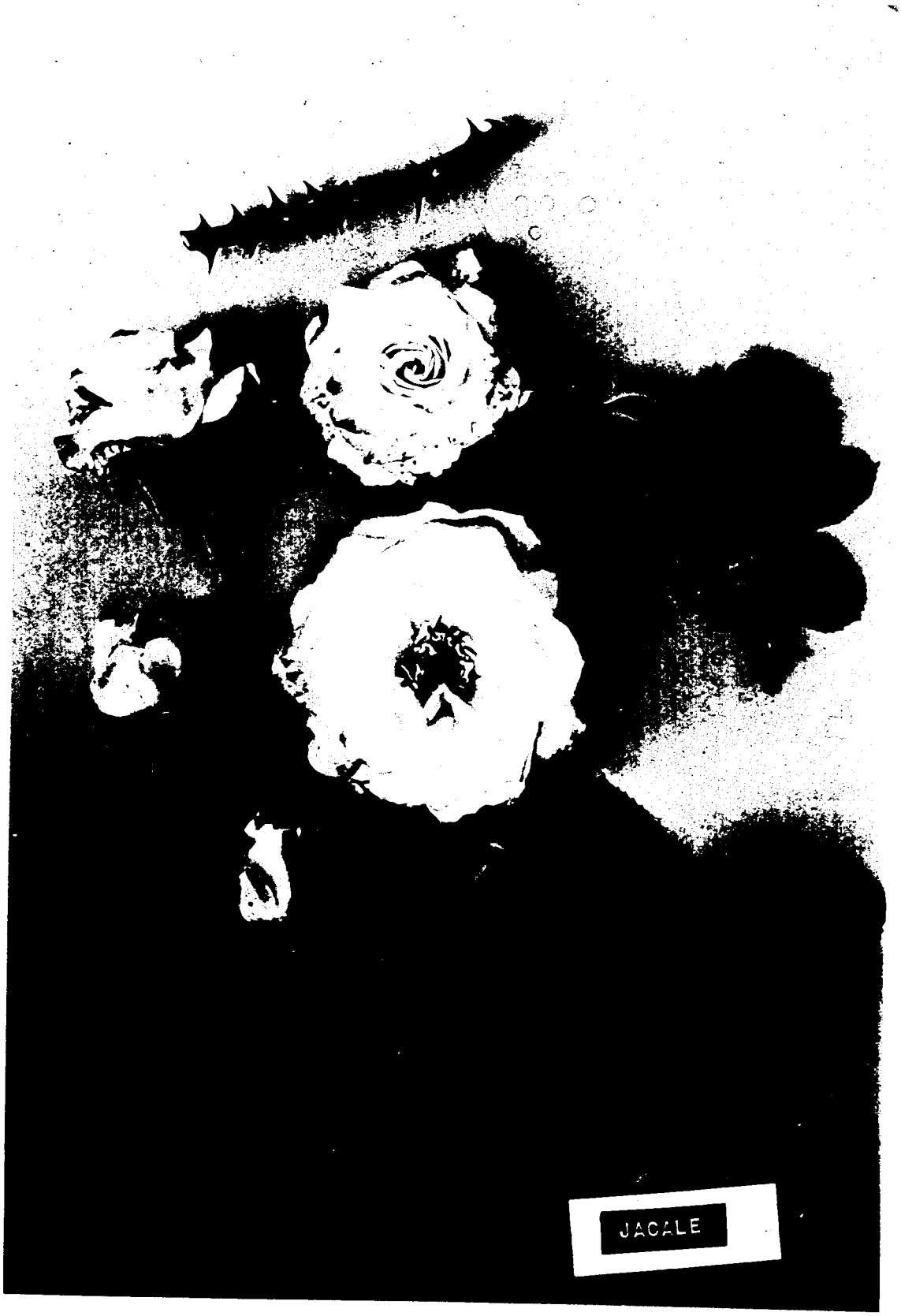
JACALE